United States Patent [19]
Sinn et al.

[11] Patent Number: 6,150,327
[45] Date of Patent: Nov. 21, 2000

[54] CONJUGATE OF AN ACTIVE AGENT, A POLYETHER AND POSSIBLY A NATIVE PROTEIN REGARDED AS ACCEPTABLE BY THE BODY

[75] Inventors: Hannsjörg Sinn, Wiesloch; Hans-Hermann Schrenk, Zeiskam; Wolfgang Maier-Borst, Dossenheim; Gerd Stehle, Mannheim, all of Germany

[73] Assignee: Deutsches Krebsforschungszentrum Stiftund des Offentlichen Rechts, Germany

[21] Appl. No.: 08/949,591

[22] PCT Filed: Apr. 12, 1996

[86] PCT No.: PCT/DE96/00653

§ 371 Date: Mar. 9, 1998

§ 102(e) Date: Mar. 9, 1998

[87] PCT Pub. No.: WO96/32134

PCT Pub. Date: Oct. 17, 1996

[30] Foreign Application Priority Data

Apr. 13, 1995 [DE] Germany .............................. 195 14 087

[51] Int. Cl.[7] .......................... A61K 38/00; A61K 38/16; C07K 1/00; C07K 7/00
[52] U.S. Cl. ............................. 514/8; 530/324; 530/403; 424/85.4
[58] Field of Search ................................... 530/324, 403; 514/8; 424/85.4

[56] References Cited

U.S. PATENT DOCUMENTS

| 4,902,502 | 2/1990 | Nitecki et al. ........................... 424/83 |
| 5,382,657 | 1/1995 | Karasiewicz et al. .................. 530/351 |

FOREIGN PATENT DOCUMENTS

| 0 473 084 | 3/1992 | European Pat. Off. . |
| 0 511 903 | 11/1992 | European Pat. Off. . |
| 0 576 192 | 12/1993 | European Pat. Off. . |
| 0 593 868 | 4/1994 | European Pat. Off. . |
| 40 17 439 | 12/1991 | Germany . |
| 44 35 087 | 4/1996 | Germany . |
| WO A 90 15059 | 12/1990 | WIPO . |
| WO A 95 29915 | 11/1995 | WIPO . |

OTHER PUBLICATIONS

Bonina et al., 1995, "In Vitro and In Vivo Evaluation of Polyoxyethylene Indomethacin Esters as Dermal Prodrugs," *Journal of Controlled Release* 34(3):223–232.

Miron et al., 1993, "A Simplified Method for the Preparation of Succinimidyl Carbonate Polyethylene Glycol for Coupling to Proteins," *Bioconjugate Chemistry* 4(6):568–569.

*Primary Examiner*—Avis M. Davenport
*Attorney, Agent, or Firm*—Pennie & Edmonds, LLP

[57] ABSTRACT

This invention relates to the use of a conjugate comprising an active substance and a native protein which is not recognized as foreign protein for the production of a pharmaceutical preparation for treating and/or diagnosing inflammatory, infectious and/or skin diseases.

10 Claims, 5 Drawing Sheets

THPP p-Tetrahydroxyphenylporphin-carboxy-PEG (THPP-PEG)

(*NPC-PEG=Nitrophenylcarbonate-PEG)

Aluminum-Phthalocyanintetrasulfonate-aminoPEG

6,150,327

CONJUGATE OF AN ACTIVE AGENT, A POLYETHER AND POSSIBLY A NATIVE PROTEIN REGARDED AS ACCEPTABLE BY THE BODY

This is a national phase filing of the Application No. PCT/DE96/00653, which was filed with the Patent Corporation Treaty on Apr. 12, 1996, and is entitled to priority of the German Patent Application 195 14 087.7, filed Apr. 13, 1995.

I. FIELD OF THE INVENTION

The present invention relates to a conjugate comprising an active substance component, a polyether component and optionally a native protein component which is not regarded as exogenous, a process for the preparation of such a conjugate as well as its use.

II. BACKGROUND OF THE INVENTION

It has long been a demand of concentrating pharmaceutical preparations in well-calculated fashion at the site of action. In particular when tumoral diseases, infectious diseases, skin diseases and/or diseases of the immune system are treated, it is desired to concentrate pharmaceutical preparations in the cells and tissues affected by these diseases. In addition, it is intended to eliminate the pharmaceutical preparations in case they do not reach the site of action. This is to serve for minimizing the strain of the body, caused by the pharmaceutical preparations.

Therefore, it is the object of the present invention to provide a possibility serving for achieving the above.

III. SUMMARY OF THE INVENTION

The present invention relates to a conjugate comprising an active substance component, a polyether component and optionally a native protein component which is not regarded as exogenous, the components being linked via an acid amide and/or acid ester bond.

In addition, this invention relates to a process for the preparation of such a conjugate as well as its use.

IV. BRIEF DESCRIPTION OF THE DRAWINGS

V. DETAILED DESCRIPTION OF THE INVENTION

Figure 1A:
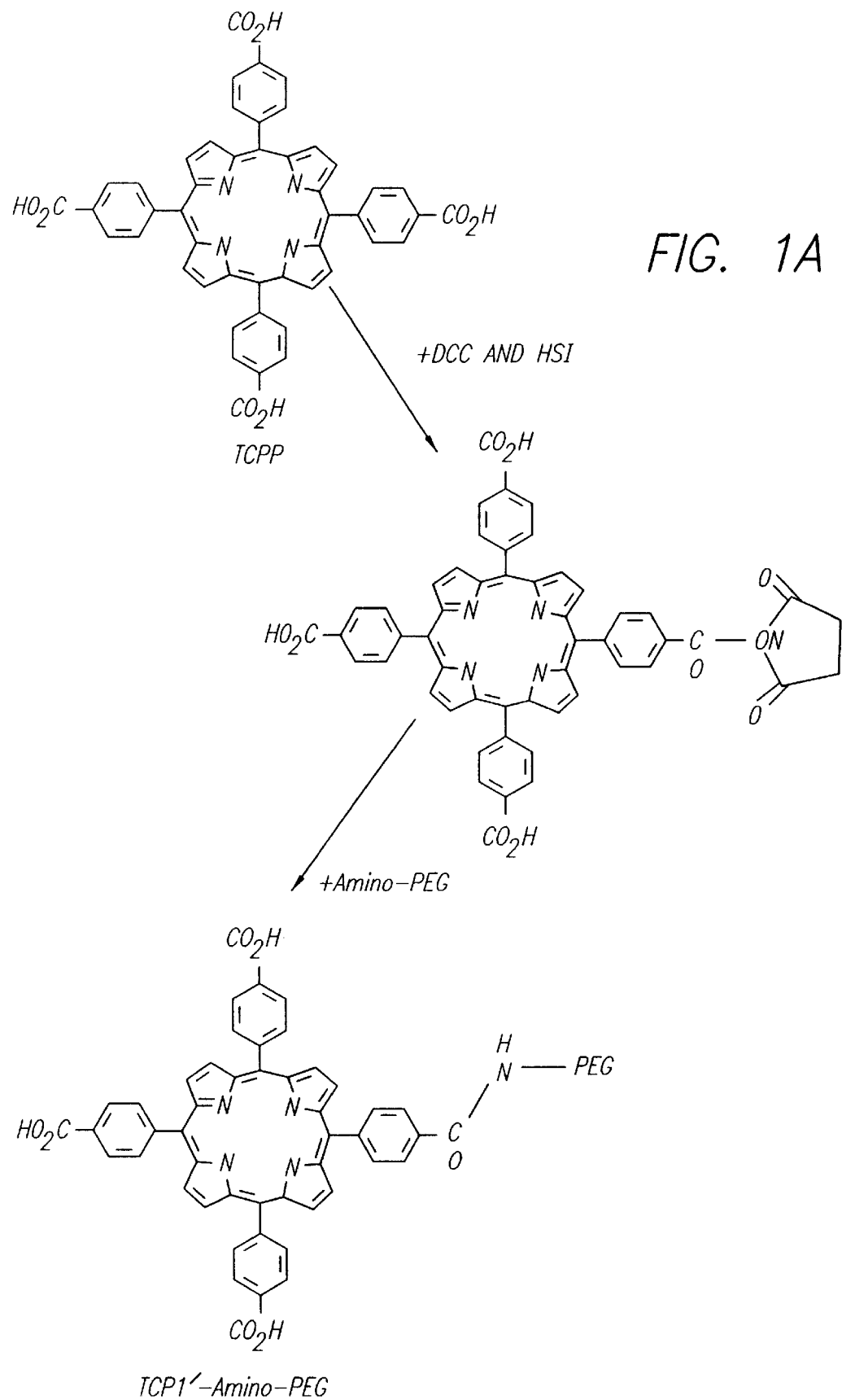
FIGS. 1A and 1B show the preparation of a conjugate according to the invention consisting of TCPP, amino PEG and HSA.

It has long been a demand of concentrating pharmaceutical preparations in well-calculated fashion at the site of action. According to the invention this is attained by a conjugate comprising an active substance component, a polyether component and optionally a native protein component not regarded as exogenous, which is characterized in that the components are linked via an acid amide and/or acid ester bond.

The components of the conjugate according to the invention are given as educts below. In the conjugate according to the invention they are present in derivatized form.

The expression "active substance" comprises compounds of any kind which can be used for treating and/or diagnosing diseases such as tumoral diseases, infectious diseases, skin diseases and/or diseases of the immune system, and which are capable of forming acid amide and/or acid ester bonds.

Such compounds may be chemotherapeutic agents, e.g., antibiotics, virostatics, antiprotozoals and cytostatic agents. Examples of antibiotics are sulfonamides, tetracyclines, e.g., 7-chlorotetracycline, fusidic acid, gyrase inhibitors, e.g., quinolones, amphotericin, isoniazid, pyrazine-2-carboxylic acid and pyrazinamide. Examples of virostatics are amantadine and rimantadine. Examples of antiprotozoals are mefloquin and primaquin. Examples of cytostatic agents are anthracyclines, e.g., doxorubicin, topoisomerase inhibitors, mitomyclin A and C, bleomycinic acid, chlorambucil, melphalan and antifolates, e.g., methotrexate.

In addition, such a compound may be a photoactive compound, particularly a photoactive compound which is photoactive in aqueous media. Examples thereof are porphyrins, such as o-, m- and/or p-tetrahydroxyphenylporphin (THPP), o-, m- and/or p-tetracarboxyphenylporphin (TCPP), and o-, m- and/or p-tetrasulfophenylporphin, clorins, such as o-, m- and/or p-tetrahydroxyphenylchlorin, o-, m- and/or p-tetracarboxyphenylchlorin, and o-, m- and/or p-tetrasulfophenylchlorin, bacteriochlorins, such as o-, m- and/or p-tetrahydroxyphenylbacteriochlorin, o-, m- and/or p-tetracarboxyphenylbacteriochlorin, and o-, m- and/or p-tetrasulfophenylbacteriochlorin, and phthalocyanines such as phthalocyaninetetrasulfonic acid. The above photoactive compounds may include metal ions such as $Al^{3+}$ or $Zn^{2+}$, which may have a positive influence on the photoactivity.

The above compounds may be provided with a detectable labeling, e.g., radioactive iodine, a metal ion such as $In^{3+}$ and/or $Gd^{3+}$. As a result, conjugates according to the invention may also be used for diagnosing diseases.

One or more of the above compounds and analogues or derivatives thereof, respectively, may be present in a conjugate according to the invention. If several are present, they may be the same or differ from one another.

A conjugate according to the invention has a polyether or a derivative thereof, which are capable of forming acid amide and/or acid ester bonds. Examples of such polyethers are polyethylene glycols (PEG), particularly those in which the terminal hydroxyl groups are esterified or etherified by a $C_1$–$C_{12}$ alkyl residue, preferably methyl. Representatives thereof are methoxypolyethylene glycol, diaminomethoxypolyethylene glycol, methoxypolyethylene glycol-p-nitrophenylcarbonate, methoxypolyethylene glycol succinimidyl succinate, methoxypolyethylene glycol tresylate, methoxypolyoxyethylene amine (aminoPEG), methoxypolyoxyethylene-carboxylic acid and methoxypolyoxyethyleneimidazole-carbonyl. The polyether preferably has a molecular weight of 100 to 20,000 daltons, especially preferably about 5,000 daltons. In addition, the polyether may be provided with an above detectable labeling.

One or more of the above polyethers are present in a conjugate according to the invention. If several are present, they may be the same or differ from one another.

A conjugate according to the invention optionally contains a native protein which is not regarded as exogenous and is capable of forming acid amide and/or acid ester bonds. This protein preferably has a molecular weight of up to 90,000 daltons. Especially preferred is the protein albumin, particularly human serum albumin (HSA), and transferrin.

The components of a conjugate according to the invention are chosen such that the molecular weight of the conjugate has preferably more than about 10,000 daltons and especially preferably more than about 15,000 daltons.

The individual components of a conjugate according to the invention may be linked as desired with one another. The active substance is preferably bound to both the polyether and the protein, if present (FIGS. 1 to 3).

Figure 1B:
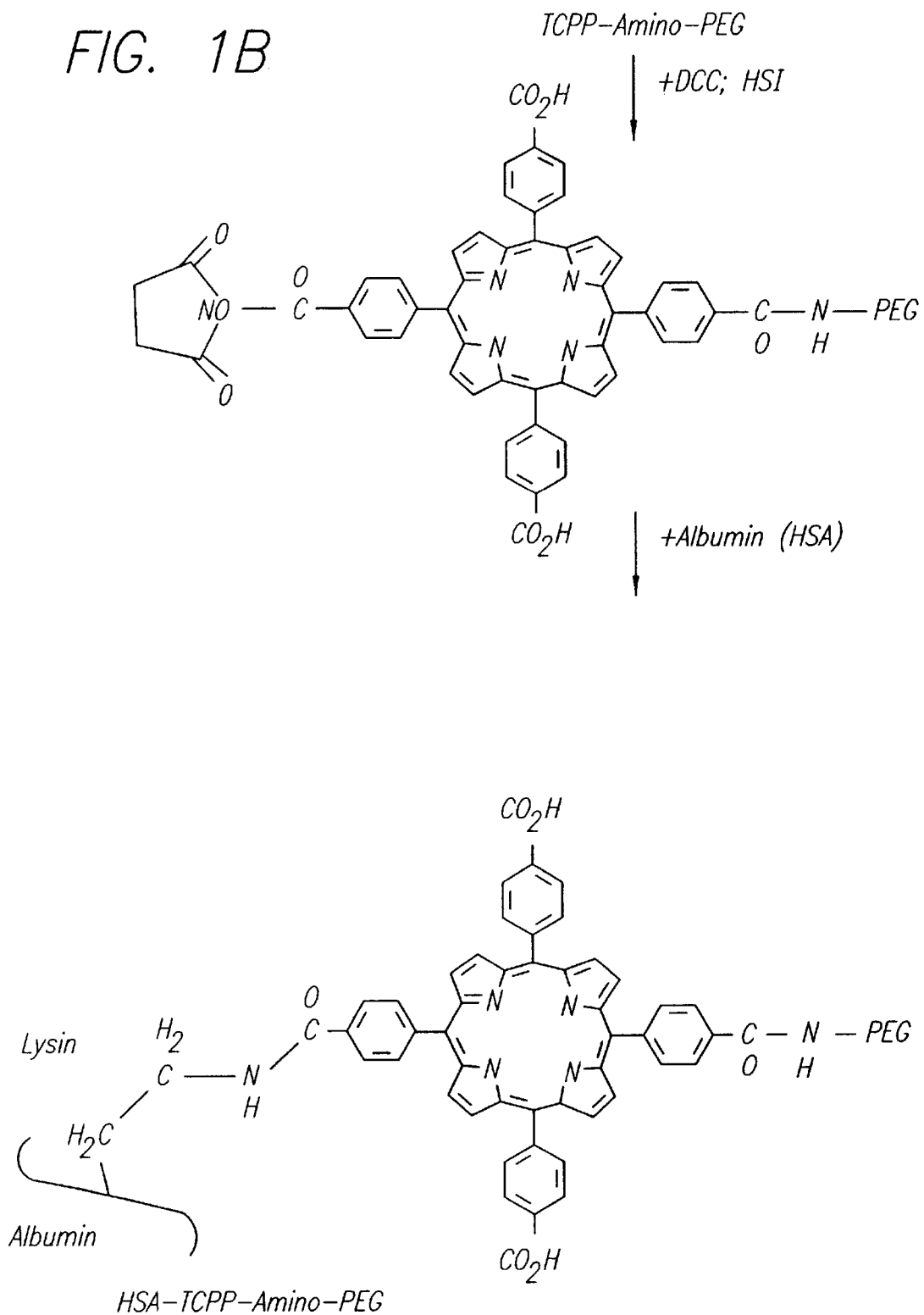
Figure 2:
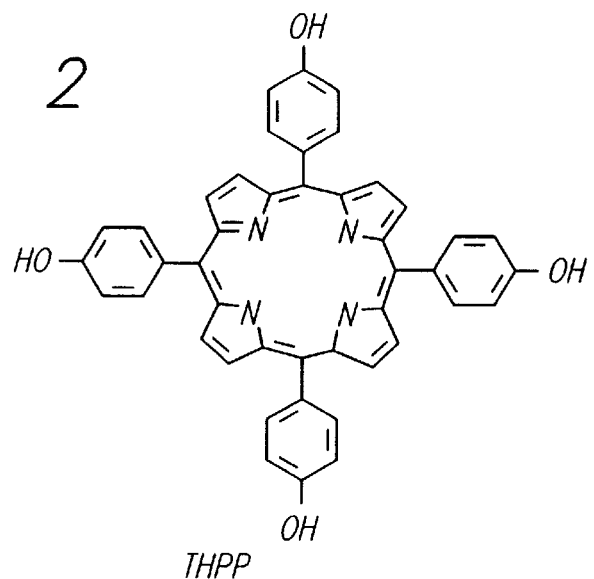
FIG. 2 shows the preparation of a conjugate according to the invention consisting of THPP and 4 PEGs.
Figure 2:
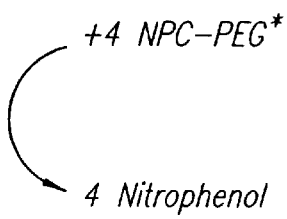
Figure 2:
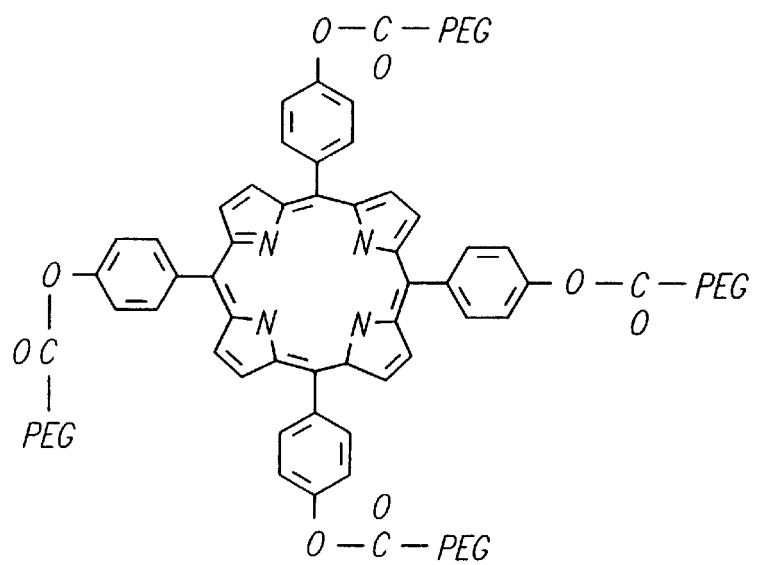
Figure 3:
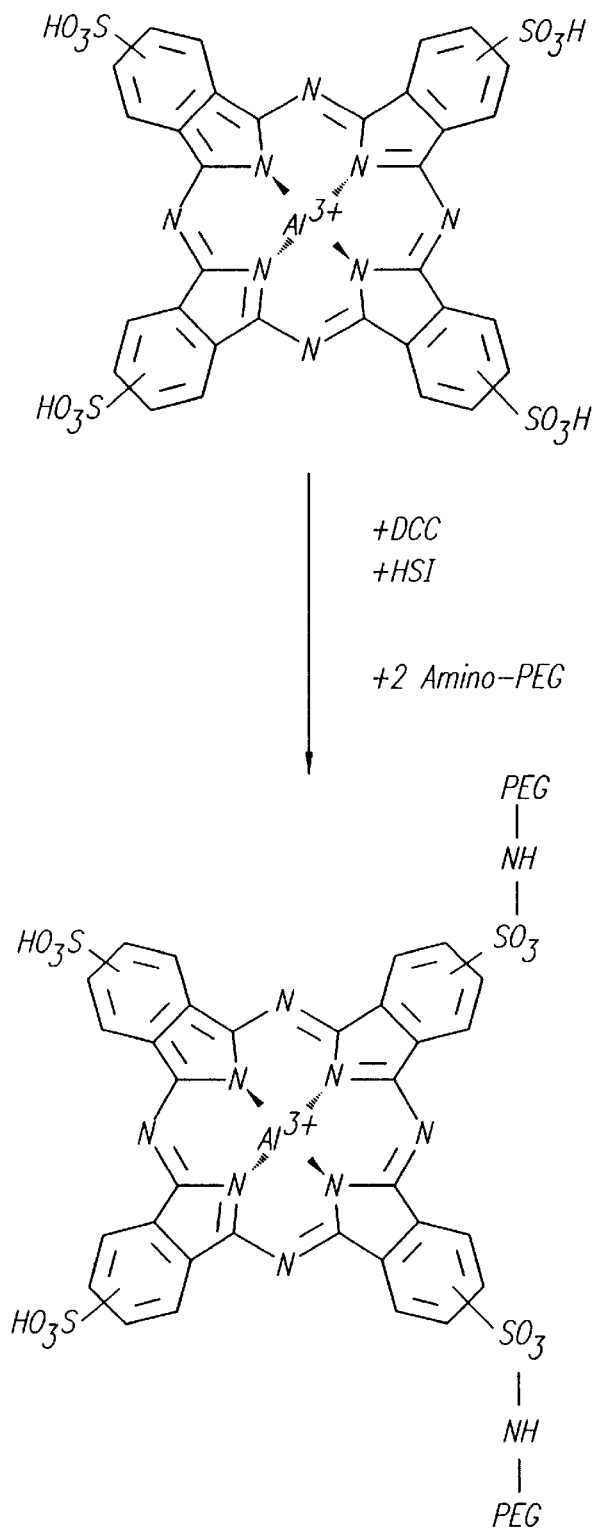
FIG. 3 shows the preparation of a conjugate according to the invention consisting of aluminum-phthalocyanintetrasulfonate-aminoPEG.

Preferred conjugates according to the invention are shown in FIGS. 1 to 3.

A process for the preparation of an above conjugate is also provided according to the invention. In such a process, conventional reactions occurring in chemistry are carried out, such as activation of an acid group and linkage of the activated acid group with an amino or hydroxyl group. For this purpose, reference is made to the preparation of the conjugates in Examples 1 and 2 as well as in FIGS. 1 to 3.

Conjugates according to the invention distinguish themselves in that they concentrate in well-calculated fashion in certain cells of the body, particularly tumor cells and cells of inflammatory tissue and pathological skin. In addition, the conjugates according to the invention distinguish themselves in that they can be degraded rapidly if they do not reach the site of action. As a result, side effects can be minimized for the body.

Conjugates according to the invention are thus suitable in the best possible manner for treating diseases, e.g., tumoral diseases, infectious diseases, skin diseases, such as psoriasis, and/or diseases of the immune systems.

Besides, conjugates according to the invention can be used—after being labeled for diagnosing diseases, particularly the above diseases.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1: Preparation of a Conjugate According to the Invention Consisting of TCPP, HSA and aminoPEG The preparation of this conjugate is shown in FIGS. 1A and 1B.

a) TCPP activation by dicyclohexylcarbodiimide (DCC) and hydroxysuccinimide (HSI) and subsequent reaction with aminoPEG TCPP (MW: 791) is dissolved in dimethylsulfoxide (DMSO) with a concentration of 10 mg/ml. Four times the molar amount of dicyclohexylcarbodiimide (DCC, MW: 206.33) and ten times the molar amount of hydroxysuccinimide (HSI, MW: 115.1) are added to the clear dark-red solution. After a reaction time of about 2 to 3 h, the conversion into TCPP-succinimidyl ester (TCPP-SE) has proceeded to such an extent that the equimolar amount of aminoPEG can be added to form TCPP-aminoPEG. After another 12 to 14 h of reaction time, the formation of TCPP-aminoPEG-HSI$_3$ is checked by means of a DPC unit.

| Running conditions: | |
|---|---|
| HPLC pump, rheodyne injection valve, UV monitor | |
| precolumn: | 30 × 8 mm, Eurogel SEC 1000, |
| column: | two 300 × 10 mm, Eurogel SEC 1000 |
| solvent: | DMF with 1 mM liBR (0.1% by mole LiBr)/L DMF |
| flow: | 0.6 mL/min |
| retention times: | |
| polystyrene standards: | 5 kD     27.00 min |
| average molecular weight: | 10 kD     24.67 min | b) Linkage of TCPP-aminoPEG to human serum albumin (HSA): The DMSO solution of amino-PEG-TCPP-SE$_3$ is added very slowly and with constant stirring to a solution of 4 g HSA$_{(20\%, immuno)}$ (dissolved in 20 ml of original solution+20 ml 0.17 M NaHCO$_3$ and 15 ml EtOH), the initially clear solution turning turbid by unreacted DCC which is insoluble in aqueous solution. After terminating the addition of aminoPEG-TCPP-SE$_x$, the reaction mixture is stirred at room temperature for another 30 min so as to complete the reaction to the greatest possible extent and then stored in a refrigerator for one hour. Thereafter, the turbid matter is separated via a sterile filter unit (Millipore, Stericup-GV, 0.22 μm Low Binding Duropore Membrane) and the low-molecular water-soluble components (DMSO, HSI and unbound TCPP) are separated by ultrafiltration via a membrane having 30 kD exclusion limit (Amicon YM 30). HSA-TCPP-aminoPEG was obtained (FIGS. 1A and 1B). The linkage yield of TCPP-aminoPEG to HSA is 85 to 90% on the average.

Analytical purity is controlled by means of HPLC.

| HPLC conditions: | |
|---|---|
| precolumn: | Zorbax Diol (50 × 4 mm) |
| column 1: | Zorbax GF 450 |
| column 2: | Zorbax GF 250 |
| eluent: | 0.2 m Na citrate, pH 7.5 |
| flow: | 1 ml/min |
| UV detector 1: | 280 nm (for the protein) |
| UV detector 2: | 420 nm (for TCPP) |
| feed volume: | 100 μl (= maximum of 10 mg protein) |
| retention times: | |
| dimeric fraction | 17.7 min. |
| monomeric fraction | 19.77 min. |

B. Example 2: Preparation of a Conjugate According to the Invention Consisting of THPP and 4 PEGs The preparation of this conjugate is shown in FIG. 2.

30 mg of 5,10,15,20-tetrakis (4-hydroxyphenyl) 21H, 23H-porphin (THPP) are dissolved in 3 ml DMF. Four times the molar excess of methoxypolyethylene glycol-p-nitrophenylcarbonate (=1 g NPC-MPEG, dissolved in 10 ml DMF) and 5 ml of bicarbonate solution (0.17 M, pH 8.5) are added thereto. The reaction takes several days for the complete conversion of the employed THPP at room temperature and can be controlled by means of HPLC. THPP-PEG (FIG. 2) was obtained.

| HPLC Conditions: Pump, rheodyne valve UV/VIS and RI detectors | | |
|---|---|---|
| precolumn: | 30 × 8 mm, Eurogel SEC 1000 (Knauer, Berlin) | |
| columns: | two columns of 300 × 10 mm each, Eurogel SEC 1000 (Knauer, Berlin) | |
| eluent: | DMF + 87 mg (1 mM) LiBr/L DMF | |
| flow: | 0.6 ml/min | |
| retention times: | | |
| polystyrene standards: | 20 KD | 23.0 min |
| | 10 KD | 24.65 min |
| | 5 KD | 27.05 min |
| molecular weight: THPP-PEG: | 22 min | |

For separating released p-nitrophenyl, unreacted mPEG and DMF, the reaction mixture is inserted in 1 L 0.05 N HCl and the accompanying substances are separated by ultrafiltration (YM 10, Amicon) from THPP-mPEG.

C. Example 3: Scintigraphic Detection of the Absorption of the HSA-TCPP-AminoPEG Conjugate by a Walker Carcinosarcoma as Compared to the Cardiac and Liver Regions A rat having a Walker carcinosarcoma was given the HSA-TCPP-aminoPEG conjugate according to the invention (FIGS. 1A and 1B). The absorption of the conjugate by the tumor was shown scintigraphically as usual and compared with the reduction in the cardiac and liver regions.

Figure 4:
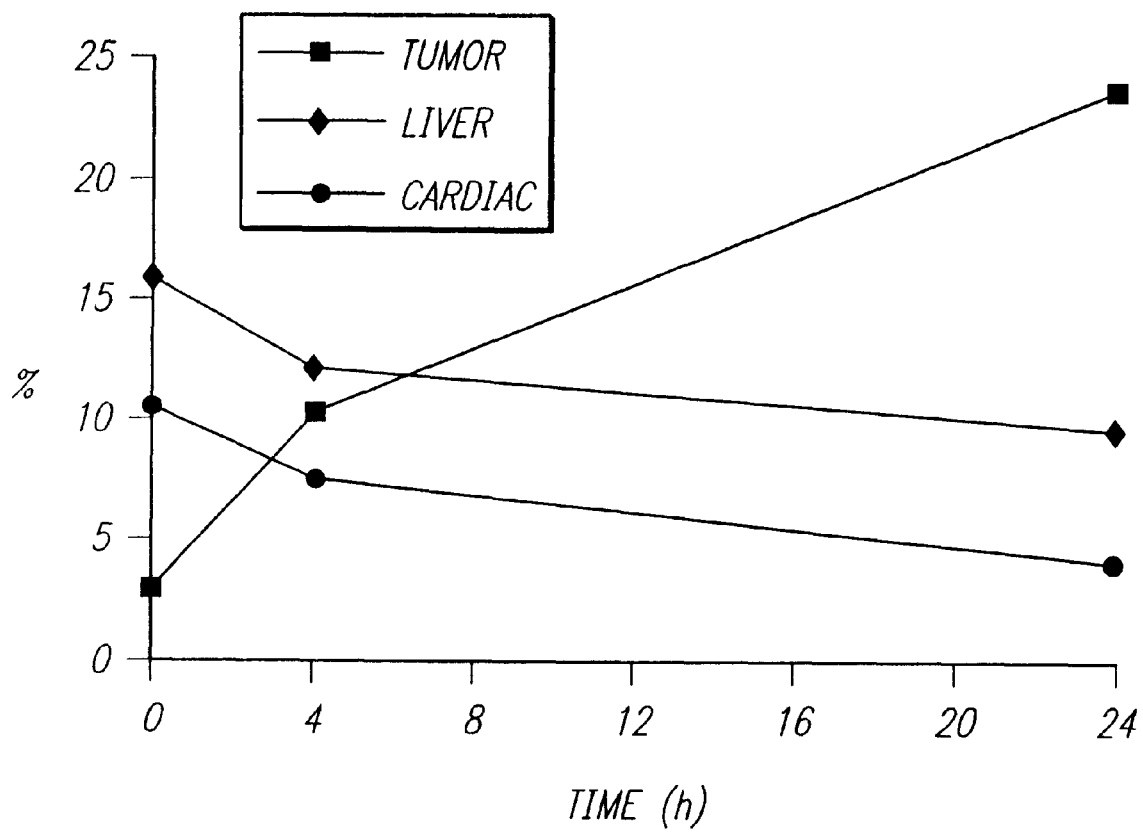
FIG. 4 shows the scintigraphic detection of the absorption of the HSA-TCPP-aminoPEG conjugate (FIGS. 1A and 1B) by a Walker carcinosarcoma as compared to the cardiac and liver regions.

As follows from FIG. 4, the conjugate according to the invention concentrates in the tumor.

All references cited within the body of the instant specification are hereby incorporated by reference in their entirety.

What is claimed:

1. A conjugate comprising an active substance component, a polyether component and a native protein component, wherein the components are linked via an acid amide and/or acid ester bond and wherein said native protein component is selected from the group consisting of albumin and transferrin.

2. The conjugate of claim 1, wherein the active substance component is a compound usable for treating a disease selected from the group consisting of a tumoral disease, infectious disease, skin disease and disease of the immune system.

3. The conjugate of claim 1, wherein the active substance component is a chemotherapeutic agent or a photoactive compound.

4. The conjugate of claim 1, wherein more than one active substance component is present.

5. The conjugate of claim 1, wherein the polyether component is a polyethylene glycol or a derivative thereof.

6. The conjugate of claim 1, wherein more than one polyether component is present.

7. A process for the preparation of the conjugate of claim 1, wherein an active substance component, a polyether component and a native protein component are linked with one another by forming acid amide and/or acid ester bonds and wherein said native protein component is selected from the group consisting of albumin and transferrin.

8. A pharmaceutical composition comprising the conjugate of claim 1 and a pharmaceutically acceptable carrier.

9. A method of treating a disease comprising administering the pharmaceutical composition of claim 8 to a human in a therapeutically effective amount.

10. The method of claim 9, wherein the disease is selected from the group consisting of a tumoral disease, an infectious disease, a skin disease and a disease of the immune system.

* * * * *